United States Patent [19]

Cerutti et al.

[11] Patent Number: 5,187,060
[45] Date of Patent: Feb. 16, 1993

[54] DETECTION OF INFLUENZA A VIRUS BY POLYMERASE CHAIN REACTION (PCR) PRECEDED BY REVERSE TRANSCRIPTION OF A REGION OF THE VIRAL HEMAGGLUTININ GENE

[75] Inventors: Peter A. Cerutti, Poly/Lausanne; Albéric Bressoud, Lausanne, both of Switzerland

[73] Assignee: Behringwerke Aktiengesellschaft, Marburg, Fed. Rep. of Germany

[21] Appl. No.: 575,601

[22] Filed: Aug. 31, 1990

[30] Foreign Application Priority Data

Sep. 2, 1989 [DE] Fed. Rep. of Germany ....... 3929144

[51] Int. Cl.$^5$ .................. C12Q 1/70; C12Q 1/68; C12Q 1/02; C07H 15/12
[52] U.S. Cl. .................................. 435/5; 435/6; 435/7.5; 435/29; 435/91; 536/23.72; 935/2; 935/16
[58] Field of Search ............ 435/6, 91, 7, 12, 5, 435/6, 7.5; 536/27

[56] References Cited

U.S. PATENT DOCUMENTS 4,357,421 11/1982 Emtage et al. ..................... 435/68
4,583,195 7/1987 Mullis et al. ........................ 435/6

OTHER PUBLICATIONS

Winter et al. Nature 292:72-75 (1981).
Sleigh et al., Nuc. Ac. Res. 7(4):879 (1979).
A. Hiti et al., "Complete Sequence Analysis Shows that the Hemagglutinins of the H0 and H2 Are Closely Related", Virology 111:113-124 (1981).
Bressoud et al., Biochemical and Biophysical Research Communications 167(2):425-30 (1990).
Rajakumar et al., Proc. Natl. Acad. Sci. USA 87:4154-58 (1990).
Saiki et al., Science 239:487-91 (1988).
Raymond et al., Nucleic Acids Research 11:20, 7191-203 (1983).
White et al., Trends in Genetics 5(6):185-89 (1989).
Cox et al., J. Gen. Virol. 70:299-313 (1989).
Kawaoka, J. Am. Vet. Med. Assoc. 194(12):1795, 185d (1989).
M. L. Perdue, J. Am. Vet. Med. Assoc. 194(12): 1795, 185e (1989).
Chomczynski and N. Sacchi, Analytical Biochemistry 162, 156-59 (1987).
Schimenti and Duncan, Nucl. Acids Res. vol. 12, No. 3 (1984).

*Primary Examiner*—Robert A. Wax
*Assistant Examiner*—Miguel Escallon
*Attorney, Agent, or Firm*—Finnegan, Henderson, Farabow, Garrett and Dunner

[57] ABSTRACT

It was possible to increase substantially the sensitivity of detection of influenza A virus by carrying out a polymerase chain reaction (PCR), using oligonucleotide sequences (amplimers) from the relatively conserved region of the viral hemagglutinin gene, preceded by reverse transcription (RT). The reverse transcription and the PCR are insensitive to single mutations by base exchange in this case, as long as the 3' end of the amplimer is not affected.

8 Claims, 1 Drawing Sheet

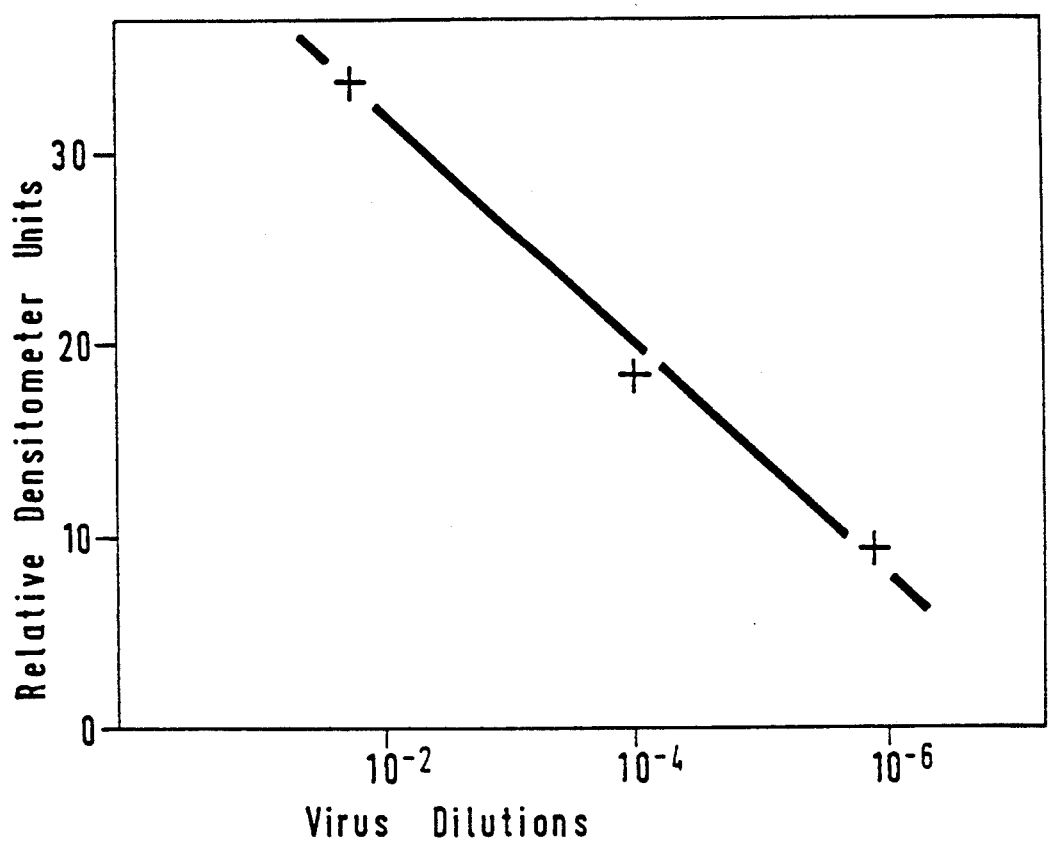

DETECTION OF INFLUENZA A VIRUS BY POLYMERASE CHAIN REACTION (PCR) PRECEDED BY REVERSE TRANSCRIPTION OF A REGION OF THE VIRAL HEMAGGLUTININ GENE

It was possible to increase substantially the sensitivity of detection of influenza A virus by carrying out a polymerase chain reaction (PCR), using oligonucleotide sequences (amplimers) from the relatively conserved region of the viral hemagglutinin gene, preceded by reverse transcription (RT). The reverse transcription and the PCR are insensitive to single mutations by base exchange in this case, as long as the 3' end of the amplimer is not affected.

The influenza A virus is found in humans and species-specifically also in animals and is the case of the pendemics which occur at relatively long intervals. The pandemics are caused by the antigenic shift of the influenza A virus. New antigenic variants against which the population is not immune develop and, for this reason, spread extremely rapidly and are associated with high mortality.

Rapid and reliable detection of influenza A virus infection is therefore very important. Generally, laboratory diagnosis is attempted by virus isolation in cell culture. However, the influenza virus can be cultured only in the first few days of the disease.

After inoculation of monkey kidney cell cultures with nasopharyngeal aspirates, viral growth becomes evident from hemadsorption of guinea pig erythrocytes. The specificity can be tested by inhibition of the hemadsorption by means of a specific immune serum. A cytopathic effect does not always occur. Some influenza virus strains can be isolated more easily by inoculation into the amniotic cavity of an embryonate chicken egg.

Experiments have been carried out to achieve rapid diagnosis for influenza: The nasopharyngeal aspirate is *smeared onto microscopic slides and the viral antigen is detected by direct or indirect immunofluorescence using specific immune sera. This test only takes a few hours but often is not sensitive enough, especially when the sample was collected late.

* for instance

Thus the object was to improve the sensitivity of the current virus detection methods for influenza A virus.

We have found that the sensitivity of the antigen detection can be substantially increased by reverse transcription and subsequent amplification by polymerase chain reaction using suitable oligonucleotides from a substantially conserved region of the viral hemagglutinin gene on the fourth segment of the viral genome. Base exchanges within the region in which the above-mentioned oligonucleotides (amplimers) are located do not interfere in this case, as long as the 3′ ends of the amplimers are not affected. The most favorable region for the reverse transcription and amplification has proved to be from position 96 to position 536 of the hemagglutinin H1 gene, but he regions ±80 nucleotides from the stated positions are also suitable. Selection of the hemagglutinin H1 gene and, in particular, of this region has the advantage that, apart from the exceptions indicated above, all serotypes of the influenza A virus are covered.

The invention therefore relates to a detection method for the influenza A virus by reverse transcription of a region of the hemagglutinin gene H1, subsequent amplification by PCR with the further use of the amplimers employed for the RT and the subsequent detection of the amplified cDNA, preferably as direct detection by staining after separation by gel electrophoresis. However, the amplified cDNA can also be detected by radioisotopes or in an ELISA, if radiolabeled or biotinylated deoxyribonucleotide tri phosphates have been employed previously. The amplimers were selected as oligonucleotides with a length of about 20 nucleotides in the region of position 96 ± 80 to 536 ± 80, preferably position 96 to 536 of the hemagglutinin gene H1. The PCR is preferably carried out at 59° C. and 91° C. and with cycle times of about one minute in each case, particularly preferably 97 sec at 59° C. and 85 sec at 91° C., in the presence of 1 mM deoxyribonucleotide triphosphates, 3% dimethyl sulfoxide and 0.8 μg of each amplimer in a total volume of 25 μl.

Finally, the invention is described in the examples and the patent claims.

EXAMPLES

1. Isolation of viral RNA

Influenza virus H1 (A/WSN/33) suspensions in PBS containing 0.2% albumin (1) or 28 nasopharyngeal lavages from presumably infected persons (2) or virus from infected cells after sonication (3) were extracted three times with acidic guanidine thiocyanate/phenol/-chloroform solution (P. Chomczynski and N. Sacchi, (1987), Analytical Biochemistry 162, 156–159). Viral RNA was precipitated at −20° C. in the presence of a t-RNA carrier (1μg/ml) by addition of 2.5 volumes of 90% buffered ethanol. After centrifugation, the precipitate was washed with 80% buffered ethanol, dried and resuspended in sterile water. The ultrasound treatment in the case of (3) was carried out for 15 sec ** paraffin oil with a Branson B15 sonicator set at 2.

** under a layer of

2. Reverse transcription

The reverse transcription was carried out at 42° C. for 30 minutes in a total volume of 5 μl. This contained 0.4 μg of each of the two amplimers, 7 U of AMV reverse transcriptase (Pharmacia) and 10 U of RNAsin (Promega) in a buffer of 50 mM Tris-HCl, pH 8.3, 50 mM KCl, 7 mM $MgCl_2$, 170 μg/ml BSA, 1 mM each of dATP, dTTP, dCTP, dGTP, 0.1% TRITON X-100, 1 mM DTT and 10 mM 2-mercaptoethanol (buffer A).

3. Amplification by PCR

The cDNA obtained above was amplified as follows: 1 U of Taq polymerase (Biofinex, Praroman, Fribourg (Switzerland)) was added to a total volume of 25 μl of buffer A without TRITON X-100 and DTT but with 3% DMSO and 0.8 μg of each amplimer.

Amplification was carried out in 30 to 40 cycles at 59° C. (96 sec in each case) and 91° C. (85 sec in each case) using an Ampligene apparatus (Moretronic, Switzerland).

4. Detection of the amplified cDNA

Detection of amplified samples was carried out in a 2% agarose gel in 10 mM Tris-HCl, pH 7.4, 0.1 mM EDTA and 0.7 μg/ml ethidium bromide under UV light.

The table shows (underlined) the position of the amplimers used, which were synthesized in a DNA synthesizer (Bio Applied Systems) and were purified through Sephadex NAP-24 columns.

The figure shows the results of a model experiment in which dilutions ($10^{-2}$ to $10^{-6}$, abscissa) of a virus suspension were plotted against the intensity of the agarose gel band with a length of 441 base pairs (bp) (ordinate). In 28 fresh nasopharyngeal lavages of possibly infected persons the 441 bp band was detected twice. A 201 bp long fragment of the cellular β-globin gene (position 717 to 926, see J. C. Schimenti and C. H. Duncan, Nucl. Acids Res. 12, (1984), 1641-1653) was coamplified as internal control in each case.

TABLE

| | | |
|---|---|---|
| 44 | CCUACUGGUCCUGUU | AUGUGCACUUGCAGC UGCAGAUGCAGACAC |
| 89 | AAUAUGU<u>AUAGGCUA</u> | <u>CCAUGCGAACAA</u>UUC AACCGACACUGUUGA |
| 134 | CACAGUACUCGAGAA | GAAUGUGACAGUGAC ACACUCUGUUAACCU |
| 179 | GCUCGAAGACAGCCA | CAACGGAAAACUAUG UAGAUUAAAAGGAAU |
| 224 | AGCCCCACUACAAUU | GGGGAAAUGUAACAU CGCCGGAUGGCUCUU |
| 269 | GGGAAACCCAGAAUG | CGACCCACUGCUUCC AGUGAGAUCAUGGUC |
| 314 | CUACAUUGUAGAAAC | ACCAAACUCUGAGAA UGGAAUAUGUUAUCC |
| 359 | AGGAGAUUUCAUCGA | CUAUGAGGAGCUGAG GGAGCAAUUGAGCUC |
| 404 | AGUGUCAUCAUUCGA | AAGAUUCGAAAUAUU UCCCAAAGAAAGCUC |
| 449 | AUGGCCCAACCACAA | CACAAACGGAGUAAC GGCAGCAUGCUCCCA |
| 494 | UGAGGGGAAAAGCAG | UUUUUACA<u>GAAAUUU</u> <u>GCUAUGGCUGACG</u>GA |
| 539 | GAAGGAGGGCUCAUA | CCCAAAGCUGAAAAA UUCUUAUGUGAACAA |

We claim:

1. A method for the detection of influenza A virus, which comprises using amplimers from the conserved region of the hemagglutinin gene H1 for reverse transcription (RT), wherein said region encompasses nucleotides in positions 96 ± 80 to 536 ± 80 of said hemagglutinin gene H1; using said amplimers in a subsequent polymerase chain reaction (PCR); and subsequently detecting the amplified cDNA by known methods.

2. The method as claimed in claim 1, wherein said amplimers are oligonucleotides with a length of about 20 nucleotides corresponding to any contiguous nucleotide sequence within the hemagglutinin gene H1 from positions 96 ± 80 to 536 ± 80.

3. The method as claimed in claim 2, wherein said amplimers are oligonucleotides of about 20 nucleotides corresponding to any contiguous nucleotide sequence within the hemagglutinin gene H1 from positions 96 ± 20 to 536 ± 20.

4. The method as claimed in claim 1, wherein said amplimers are AUAGGCUACCAUGCGAACAA and GAAAUUUGCUAUGGCUGACG.

5. A reagent composition for the detection of influenza A virus, said composition containing amplimers from the conserved region of the hemagglutinin gene H1, said region encompassing nucleotides in positions 96 ± 80 to 536 ± 80 of said hemagglutinin gene H1, for use in a reverse transcription and subsequent polymerase chain reaction.

6. A reagent composition as claimed in claim 5, wherein the amplimers contain about 20 nucleotides corresponding to any contiguous nucleotide within the hemagglutinin gene H1 from positions 96 ± 80 to 536 ± 80.

7. A reagent composition as claimed in claim 5, wherein the amplimers contain about 20 nucleotides corresponding to any contiguous nucleotide sequence within the hemagglutinin gene H1 from positions 96 ± 20 to 536 ± 20.

8. A reagent composition as claimed in claim 5, wherein said amplimers are AUAGGCUACCAUGCGAACAA and GAAAUUUGCUAUGGCUGACG.

* * * * *